United States Patent
Steenbakkers

(10) Patent No.: US 7,320,873 B2
(45) Date of Patent: Jan. 22, 2008

(54) USE OF ANTIBODIES AGAINST SPECIFIC MHC-PEPTIDE COMPLEXES

(75) Inventor: Petrus Gerardus Antonius Steenbakkers, Wethouder Donkerstraat (NL)

(73) Assignee: N.V. Organon, Oss (NL)

( * ) Notice: Subject to any disclaimer, the term of this patent is extended or adjusted under 35 U.S.C. 154(b) by 500 days.

(21) Appl. No.: 10/344,872

(22) PCT Filed: Aug. 8, 2001

(86) PCT No.: PCT/EP01/09136

§ 371 (c)(1),
(2), (4) Date: Feb. 14, 2003

(87) PCT Pub. No.: WO02/14870

PCT Pub. Date: Feb. 21, 2002

(65) Prior Publication Data

US 2004/0137514 A1     Jul. 15, 2004

(51) Int. Cl.
G01N 33/564 (2006.01)
G01N 33/563 (2006.01)
C07K 16/28 (2006.01)

(52) U.S. Cl. ............ 435/7.21; 530/388.2; 530/388.22; 530/389.1; 530/866; 530/868

(58) Field of Classification Search ................ 435/7.21; 530/388.22, 389.1, 868; 424/130.1, 152.1, 424/810
See application file for complete search history.

(56) References Cited

U.S. PATENT DOCUMENTS 6,020,170 A    2/2000  Steenbakkers

FOREIGN PATENT DOCUMENTS

| EP | 488470 | 6/1992 |
| WO | 95 01995 A | 1/1995 |
| WO | 95 02188 A | 1/1995 |

OTHER PUBLICATIONS

Wicks, I et al (Ann. Rheum. Dis. [1997] 56:135-139.*
Tisch, R et al. Proc. Nat. Acad. Sci. (USA). [1994] 91:437-438.*
Harvey S et al: "Chondrex: New Marker of Joint Disease"; Clinical Chemistry, American Association for Clinical Chemistry, Winston, US, vol. 44, No. 3, Mar. 1998, pp. 509-516.
Verheijden G F M et al: "Human Cartilage Glycoprotein-39 as a Candidate Autoantigen in Rheumatoid Arthritis"; Arthritis and Rheumatism, Lippincott, Philadelphia, US, vol. 40, No. 6, Jun. 1997, pp. 1115-1125.
Porgador A et al: "Localization Quantitation, and in SITU Detection of Specific Peptide-MHC Class I Complexes using a Monoclonal Antibody"; Immunity, Cell Press, US, vol. 6, No. 6, Jun. 1997, pp. 715-726.
Adang et al., "Case Histories of Peptidomimetics: Progression from Peptides to Drugs," Recl. Trav. Chim. Pays-Bas 113 (1994) 63-78.
Altman et al., "Phenotypic Analysis of Antigen-Specific T Lymphocytes," Science 274 (1996) 94-96.
Baeten et al, "Detection of Major Histocompatibility Complex/Human Cartilage gp-39 Complexes in Rheumatoid Arthritis Synovitis as a Specific and Independent Histologic Marker," Arthritis Rheum. 50 (2004) 444-451.

(Continued)

Primary Examiner—Christina Chan
Assistant Examiner—F. Pierre VanderVegt
(74) Attorney, Agent, or Firm—Susan Hess

(57) ABSTRACT

The invention describes a method to diagnose the autoimmune disease activity by detecting the presence of an autoimmune specific MHC-peptide complex in a patient suffering from an autoimmune disease. The MHC-peptide complex is associated with rheumatoid arthritis. Monoclonals antibodies to be used for this method are also described. The antibodies can also be used for therapeutic purposes.

14 Claims, 8 Drawing Sheets

OTHER PUBLICATIONS

Figure 1:
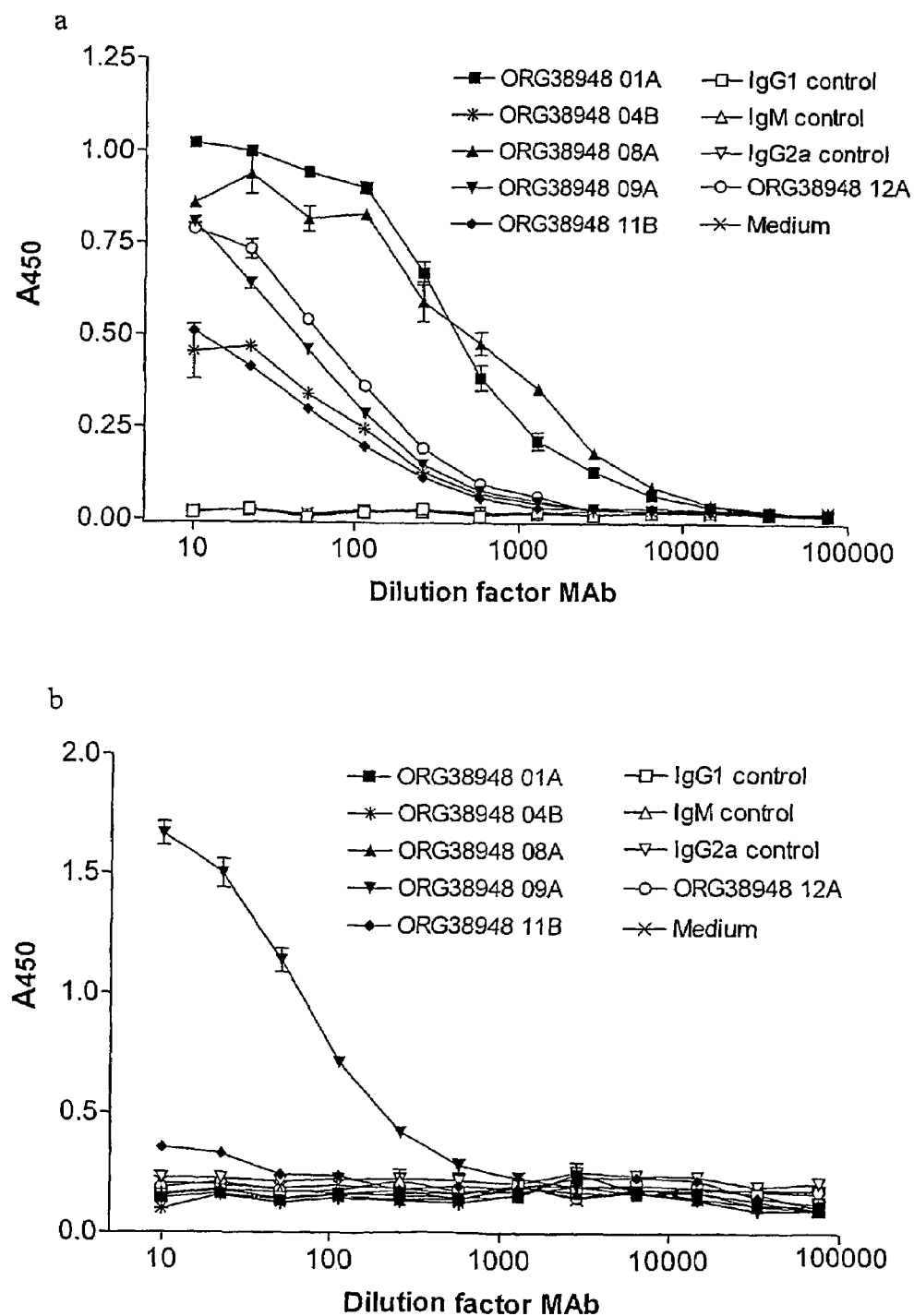

Baeten et al., "Human Cartilage gp-39+, CD16+ Monocytes in Peripheral Blood and Synovium," *Arthritis Rheum* 43 (2000) 1233-1243.

Cope et al., "T Cell Responses to a Human Cartilage Autoantigen in the Context of Rheumatoid Arthritis-Associated and Nonassociated HIA-DR4 Alleles," *Arthritis Rheum.* 42 (1999) 1497-1507.

Fields et al., "Solid Phase Peptide Synthesis Utilizing 9-fluorenylmethoxycarbonyl amino acids," *Int. J. Peptide Protein Res.* 35 (1990) 161-214.

Gütgemann et al., "Induction of Rapid T Cell Activation and Tolerance by Systemic Presentation of an Orally Administered Antigen," *Immunity* 8 (1998) 667-673.

Jones et al., "Replacing the Complementarity-Determining Regions In a Human Antibody With those from a Mouse," *Nature* 321 (1986) 522-525.

Joosten et al., "Induction of Tolerance With Intranasal Administration of Human Cartilage gp-39 In DBA/1 Mice," *Arthritis Rheum.* 43, (2000) 645-655.

Köhler et al., "Continuous Cultures of Fused Cells Secreting Antibody of Predefined Specificity," *Nature* 256 (1975) 495-497.

Kotzin et al., "Use of soluble peptide-DR4 tetramers to detect synovial T cells specific for cartilage antigens in patients with rheumatoid arthritis," *PNAS* 97 (2000) 291-296.

Lebowitz et al., "Soluble, High-Affinity Dimers of T-Cell Receptors and Class II Major Histocompatibility Complexes: BIochemical Probes for Analysis and Modulation of Immune Responses," *Cellular Immunology* 192 (1999) 175-184.

Lipman et al., "Rapid and Sensitive Protein Similarity Searches," *Science* 227, (1985) 1435-1441.

Merrifield, "Solid Phase Peptide Synthesis. I. The Synthesis of a Tetrapeptlde," *J. Amer. Chem. Soc.* 85 (1963) 2149-2154.

Powell et al., "Peptide Stability in Drug Development: A Comparison of Peptide Reactivity in Different Biological Media," *J. Pharm. Sci.* 81 (1992) 731-735.

Simon et al., "Peptoids: A modular approach to drug discovery," *PNAS* 89 (1992) 9367-9371.

Steenbakkers et al., "A New Approach to the Generation of Human or Murine Antibody Producing Hybridomas," *J. Immunol. Methods* 152 (1992) 69-77.

Steenbakkers et al., "Efficient Generation of Monocional Antibodies from Preselected Antigen-Specific B Cells," *Molecular Biology Reports* 19 (1994) 125-134.

Van Duijn et al., "High Yields of Specific Hybridomas Obtained by Electrofusion of Murine Lymphocytes Immunized in Vivo or in Vitro," *Exp. Cell Research* 183 (1989) 463-472.

Nag et al., "Purified β-Chain of MHC Class II Binds to CD4 Molecules on Transfected HeLa Cells," *J. Immunol.* 150 (1993) 1358-1364.

* cited by examiner

SEQUENCE LISTING

<160> NUMBER OF SEQ ID NOS: 20

<210> SEQ ID NO 1
<211> LENGTH: 11
<212> TYPE: PRT
<213> ORGANISM: Homo sapiens
<220> FEATURE:
<221> NAME/KEY: misc_feature
<223> OTHER INFORMATION: HC gp-39 AA 263-273

<400> SEQUENCE: 1

Arg Ser Phe Thr Leu Ala Ser Ser Glu Thr Gly

```
1               5                   10
```

<210> SEQ ID NO 2
<211> LENGTH: 13
<212> TYPE: PRT
<213> ORGANISM: Homo sapiens
<220> FEATURE:
<221> NAME/KEY: misc_feature
<223> OTHER INFORMATION: HC gp-39 AA 263-275

<400> SEQUENCE: 2

```
Arg Ser Phe Thr Leu Ala Ser Ser Glu Thr Gly Val Gly
1               5                   10
```

<210> SEQ ID NO 3
<211> LENGTH: 12
<212> TYPE: PRT
<213> ORGANISM: Homo sapiens
<220> FEATURE:
<221> NAME/KEY: misc_feature
<223> OTHER INFORMATION: HC gp-39 AA 263-274

<400> SEQUENCE: 3

```
Arg Ser Phe Thr Leu Ala Ser Ser Glu Thr Gly Val
1               5                   10
```

<210> SEQ ID NO 4
<211> LENGTH: 10
<212> TYPE: PRT
<213> ORGANISM: Homo sapiens
<220> FEATURE:
<221> NAME/KEY: misc_feature
<223> OTHER INFORMATION: HC gp-39 AA 263-272

<400> SEQUENCE: 4

```
Arg Ser Phe Thr Leu Ala Ser Ser Glu Thr
1               5                   10
```

<210> SEQ ID NO 5
<211> LENGTH: 11
<212> TYPE: PRT
<213> ORGANISM: Homo sapiens
<220> FEATURE:
<221> NAME/KEY: misc_feature
<223> OTHER INFORMATION: HC gp-39 AA 265-275

<400> SEQUENCE: 5

```
Phe Thr Leu Ala Ser Ser Glu Thr Gly Val Gly
1               5                   10
```

<210> SEQ ID NO 6
<211> LENGTH: 10
<212> TYPE: PRT
<213> ORGANISM: Homo sapiens
<220> FEATURE:
<221> NAME/KEY: misc_feature
<223> OTHER INFORMATION: HC gp-39 AA 266-275

<400> SEQUENCE: 6

```
Thr Leu Ala Ser Ser Glu Thr Gly Val Gly
1               5                   10
```

<210> SEQ ID NO 7
<211> LENGTH: 11
<212> TYPE: PRT
<213> ORGANISM: Homo sapiens
<220> FEATURE:
<221> NAME/KEY: misc_feature

```
<223> OTHER INFORMATION: HC gp-39 AA 264-274

<400> SEQUENCE: 7

Ser Phe Thr Leu Ala Ser Ser Glu Thr Gly Val
1               5                   10

<210> SEQ ID NO 8
<211> LENGTH: 9
<212> TYPE: PRT
<213> ORGANISM: Homo sapiens
<220> FEATURE:
<221> NAME/KEY: misc_feature
<223> OTHER INFORMATION: HC gp-39 AA 265-273

<400> SEQUENCE: 8

Phe Thr Leu Ala Ser Ser Glu Thr Gly
1               5

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:  At the
                        N-terminus connected to acetyl

<400> SEQUENCE: 9

Arg Ser Phe Thr Leu Ala Ser Ser Glu Thr Gly Val Gly
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:  At the
                        N-terminus connected to HOCH2- (CHOH) 4-CH2

<400> SEQUENCE: 10

Arg Ser Phe Thr Leu Ala Ser Ser Glu Thr Gly Val Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence:  At the
                        N-terminue acteyl is connected; at the
                        C-terminus NH2 is connected
<220> FEATURE:
<221> NAME/KEY: MISC_FEATURE
<222> LOCATION: (12)..(12)
<223> OTHER INFORMATION: Xaa at position 12 is NH-CH (CH(CH3)2) -CH2

<400> SEQUENCE: 11

Arg Ser Phe Thr Leu Ala Ser Ser Glu Thr Gly Xaa Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence:  At the
                        N-terminus acetyl is connected; at the
                        C-terminus NH2 is connected
<220> FEATURE:
<221> NAME/KEY: MISC_FEATURE
```

```
<222> LOCATION: (2)..(2)
<223> OTHER INFORMATION: Xaa at position 2 is N[(CH2) 2-OH]-CH2-C (O)

<400> SEQUENCE: 12

Arg Xaa Phe Thr Leu Ala Ser Ser Glu Thr Gly Val Gly
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence:  At the
                        N-terminus acetyl is connected; at the
                        C-terminus NH2 is connected
<220> FEATURE:
<221> NAME/KEY: MISC_FEATURE
<222> LOCATION: (2)..(2)
<223> OTHER INFORMATION: Xaa at position 2 is n[CH2O2-OH]-CH2-C(O)
<220> FEATURE:
<221> NAME/KEY: MISC_FEATURE
<222> LOCATION: (12)..(12)
<223> OTHER INFORMATION: Xaa at position 12 is NH-CH(CH(CH)3)2)-CH2

<400> SEQUENCE: 13

Arg Xaa Phe Thr Leu Ala Ser Ser Glu Thr Gly Xaa Gly
 1               5                  10

<210> SEQ ID NO 14
<211> LENGTH: 14
<212> TYPE: PRT
<213> ORGANISM: Homo sapiens
<220> FEATURE:
<221> NAME/KEY: misc_feature
<223> OTHER INFORMATION: HC gp-39 AA 261-275

<400> SEQUENCE: 14

Phe Gly Arg Ser Thr Leu Ala Ser Ser Glu Thr Gly Val Gly
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:  At the
                        N-terminus acetyl is connected; at the
                        C-terminus NH2 is connected

<400> SEQUENCE: 15

Arg Ser Phe Thr Leu Ala Ser Ser Glu Thr Gly Val Gly
 1               5                  10

<210> SEQ ID NO 16
<211> LENGTH: 13
<212> TYPE: PRT
<213> ORGANISM: Influenza virus
<220> FEATURE:
<221> NAME/KEY: misc_feature
<223> OTHER INFORMATION: Haemagglutinin AA 307-319

<400> SEQUENCE: 16

Pro Lys Phe Val Lys Gln Asn Thr Leu Lys Leu Ala Thr
 1               5                  10

<210> SEQ ID NO 17
<211> LENGTH: 14
<212> TYPE: PRT
<213> ORGANISM: Mycobacterium leprae
```

-continued

```
<220> FEATURE:
<221> NAME/KEY: misc_feature
<223> OTHER INFORMATION: 18K protein AA 38-51

<400> SEQUENCE: 17

Glu Glu Phe Val Val Glu Phe Asp Leu Pro Gly Ile Lys Ala
1               5                   10

<210> SEQ ID NO 18
<211> LENGTH: 14
<212> TYPE: PRT
<213> ORGANISM: Homo sapiens
<220> FEATURE:
<221> NAME/KEY: misc_feature
<223> OTHER INFORMATION: HC gp-39 AA 106-116
<220> FEATURE:
<221> NAME/KEY: misc_feature
<223> OTHER INFORMATION: HC gp-39 AA 103-116

<400> SEQUENCE: 18

Ser Gln Arg Phe Ser Lys Ile Ala Ser Asn Thr Gln Ser Arg
1               5                   10

<210> SEQ ID NO 19
<211> LENGTH: 13
<212> TYPE: PRT
<213> ORGANISM: Homo sapiens
<220> FEATURE:
<221> NAME/KEY: misc_feature
<223> OTHER INFORMATION: HC gp-39 AA 259-271

<400> SEQUENCE: 19

Pro Thr Phe Gly Arg Ser Phe Thr Leu Ala Ser Ser Glu
1               5                   10

<210> SEQ ID NO 20
<211> LENGTH: 13
<212> TYPE: PRT
<213> ORGANISM: Homo sapiens
<220> FEATURE:
<221> NAME/KEY: misc_feature
<223> OTHER INFORMATION: HC gp-39 AA 326-338

<400> SEQUENCE: 20

Val Gly Tyr Asp Asp Gln Glu Ser Val Lys Ser Lys Val
1               5                   10
```

USE OF ANTIBODIES AGAINST SPECIFIC MHC-PEPTIDE COMPLEXES

FIELD OF THE INVENTION

The current invention relates to a method to diagnose autoimmune diseases, monoclonal antibodies used in this method, a diagnostic composition comprising these antibodies as well as a method to treat autoimmune disorders.

BACKGROUND OF THE INVENTION

Autoimmune diseases are a major problem in human health care. Some autoimmune diseases may be the result of an immunological process directed at one antigen or antigenic complex whereas in others the autoimmune reaction may involve many types of antigens that may be present in multiple organs.

The primary functional role of the immune system is to protect the individual against invading pathogens bearing foreign, that is non-self, antigens. In order to fulfil this function in a safe and effective manner, a mechanism is required to discriminate between foreign antigens and autoantigens derived from the individuals own body. Most individuals are in general tolerant to substances which occur in their own body.

Some individuals on the other hand fail to recognize their antigens as self and generate an immune response against endogenous substances, tissues, or components. Such an immune response causes great damage to the organs which contain these endogenous substances. The development of the associated autoimmune disease is in general very slow (a matter of years) and this hampers timely clinical diagnosis and treatment to a high degree. Diagnosis can generally only be made after appreciable damage has already been caused to the body.

The diagnosis of autoimmune diseases such as rheumatoid arthritis (RA) is most difficult in early disease or when relatively few joints are involved and unfortunately diagnosis is usually delayed several months after the onset of symptoms. Distinguishing e.g. rheumatoid arthritis from other causes of chronic inflammatory arthritis or transient synovitis syndromes at this point is difficult. Patients with a persistent undifferentiated polyarthritis syndrome are frequently seen and differentiation from rheumatoid arthritis may initially be difficult. Many patients will present with signs and symptoms of inflammatory arthritis but do not have rheumatoid arthritis.

The chances of individuals to develop an autoimmune disease are closely linked to their genetic backgrounds: genes encoding major histocompatibility complex (MHC) class II molecules that present (auto)antigens to responding T cells which recognize MHC-peptide complexes show a strong genetic linkage to disease susceptibility. In early disease the pathogenesis is thought to be T cell mediated. T cells recognize specific major histocompatibility complex molecules combined with antigenic peptide by virtue of the T-cell receptor (TCR). The signal generated by the MHC/peptide/TCR complex leads to T cell activation. This trimolecular complex is a key element in the general immune response and in autoimmunity. It is currently believed that the presentation of MHC-bound processed autoantigens to the TCR of CD4$^+$ T cells is involved in the pathogenesis of many autoimmune diseases.

One of the candidate autoantigens identified in rheumatoid arthritis is human cartilage glycoprotein-39 (HC gp-39) (Verheijden et al., 1997, Arthritis and Rheum., 40:1115-1125). Immunisation of BALB/c mice with this protein resulted in the development of a chronic, relapsing arthritis. Intranasal administration of the protein prior to this immunization resulted in: i) complete abrogation of DTH responses, and ii) protection from or delayed onset of the disease. Furthermore, HC gp-39 could reduce the is incidence and severity of collagen type II induced arthritis in DBA/1 mice using a semi-therapeutic regime (Joosten et al., 2000, Arthritis Rheum. 43:645-655).

Several peptides of HC gp-39 were identified as potentially self-reactive. At least four of these peptides (103-116, 259-271, 263-275 and 326-338) are recognized by T cells of RA patients. Interestingly, HC gp-39$^{263-275}$ was more prominently recognized in RA patients than in healthy controls, suggesting a role for this T-cell epitope in initiation or maintenance of rheumatoid arthritis. This peptide is therefore of interest for therapeutic and diagnostic purposes in RA. For therapeutic purposes, the peptide or a modification can be used for nasal tolerization. Furthermore, the peptide complexed with DRB1*0401 can be used for intravenous tolerization.

The peptide complexed to a MHC molecule can be exploited for diagnostic purposes. The conventional way to detect specific MHC-peptide complexes relies on the activation of T cells bearing relevant TCR. However, such functional assays cannot be used to identify TCR-ligand-bearing APC in tissue sections.

According to the present invention antibodies have been generated having specificity for a MHC-peptide complex associated with an autoimmune disease, preferably rheumatoid arthritis. Most preferred is a peptide in the complex derived from HC gp-39.

MHC-peptide complexes are syndrome-specific, i.e. the disease is characterized by the occurrence of such specific complexes of MHC and autoantigen.

SUMMARY OF THE INVENTION

It has now been found that these specific complexes can often be detected in the tissue of a patient before the clinical diagnosis can be made with certainty. The immune complexes therefore predict which disease is developing.

The timely detection of these immune complexes in the patient's tissue or blood is the more important because the patient's treatment can then be initiated earlier, thereby delaying, or even preventing, the often serious damage during the later phase of the disease.

Thus, according to one aspect of the invention a method is provided for diagnosing an autoimmune disease. The method comprises the detection of the presence of an autoimmune specific MHC-peptide complex in a patient suffering from an autoimmune disease. The detection makes use of antibodies which specifically bind to the MHC-peptide complex.

DETAILED DESCRIPTION OF THE INVENTION

The term antibody as used herein is defined as a single antibody species or multiple antibody species with binding characteristics for the relevant antigen. The antibody only recognizes the MHC-peptide complex and does not recognize the peptide or the MHC alone. Thus, the antibody must be capable of recognizing a specific autoimmune associated peptide located within the binding groove of a MHC molecule. The antibody can be purified from serum containing such antibodies but preferably the antibody is a monoclonal antibody, more preferably a mouse or human monoclonal antibody. The antibody thus binds to an autoimmune specific MHC-peptide complex in a patient suffering from an autoimmune disease. This specific complex is further referred to as MHC-peptide complex.

It will be clear to those skilled in the art that also fragments of the antibody still capable of binding to the specific MHC-peptide complex form part of the invention. By the term fragment therefore is meant those parts of the antibodies comprising variable domain regions such as Fab, F(ab')$_2$ or Fv. The antibody might also be genetically engineered including single-chain antibodies or chimeric (e.g. bi-specific) antibodies that can bind to the MHC-peptide complex. Furthermore, the antibody might consist of regions originating from different species, such as e.g. chimeric or humanized antibodies.

The MHC-peptide complex to be detected according to the present invention is associated with autoimmune diseases, preferably with rheumatoid arthritis. Preferably, the MHC complex is of the type HLA DRB1*0401, DRB1*0404, DRB1*0407 and DRB1*0101, HLA DRB1*0401 being the most preferred whereas the peptide in the complex is preferably a RA associated antigen. Preferably the antibodies are prepared using complexes with peptide derived from HC gp-39. Preferably the peptide comprises the amino acids 263-273 or 263-275 of HC gp-39 (HC gp-39$^{263-273}$ or HC gp-39$^{263-275}$), but small variations in the amino acid sequences are possible. Such antibodies will detect HC gp-39 associated MHC-peptide complexes, most likely the antibodies will detect MHC-peptide complexes the peptide of which is HC gp-39 derived.

It will be clear to those skilled in the art that the peptides may be extended at either side of the peptide or at both sides and still exert the same immunological function i.e. in a MHC associated complex it is capable to be recognized by the antibody. The extended part may be an amino acid sequence similar to the natural sequence of the protein. However, the peptide might also be extended by non-natural sequences. Also the sequence of the peptide itself might be slightly different while still capable of being recognized by the antibody.

Variations that can occur in a sequence, especially of smaller peptides, may be demonstrated by (an) amino acid difference(s) in the overall sequence or by deletions, substitutions, insertions, inversions or additions of (an) amino acid(s) in said sequence. Amino acid substitutions that are expected not to essentially alter biological and immunological activities have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science, 227: 1435-1441, 1985) and determining the functional similarity between homologous polypeptides.

The (smaller) peptides can be prepared by well known organic chemical methods for peptide synthesis such as, for example, solid-phase peptide synthesis described for instance in J. Amer. Chem. Soc. 85:2149 (1963) and Int. J. Peptide Protein Res. 35:161-214 (1990).

The peptides may be stabilised by C- and/or N-terminal modifications, which will decrease exopeptidase catalysed hydrolysis. The modifications may include: C-terminal acylation, (e.g. acetylation=Ac-peptide), N-terminal amide introduction, (e.g. peptide-NH$_2$) combinations of acylation and amide introduction (e.g. Ac-peptide-NH$_2$) and introduction of D-amino acids instead of L-amino acids (Powell et al., J. Pharm. Sci., 81:731-735, 1992).

Other modifications are focussed on the prevention of hydrolysis by endopeptidases. Examples of these modifications are: introduction of D-amino acids instead of L-amino acids, modified amino acids, cyclisation within the peptide, introduction of modified peptide bonds, e.g. reduced peptide bonds ψ[CH$_2$NH] and e.g. peptoids (N-alkylated glycine derivatives) (Adang et al., Recl. Trav. Chim. Pays-Bas, 113:63-78, 1994 and Simon et al., Proc. Natl. Acad. Sci. USA, 89:9367-9371, 1992).

Monoclonal antibodies can be prepared according to standard procedures. Immunizations of animals with MHC-peptide complex-containing preparations are performed either in the presence or absence of an appropriate adjuvant. Then, hybridomas are generated by fusion of B cells from these immunized animals with myeloma cells using an appropriate fusion technique, preferably PEG-fusion (Kohler and Milstein, Nature 256; 495-497, 1975) or electrofusion (Van Duijn et al., Exp. Cell Research, 183, 463-472, 1989). Standard procedures for immunization, fusion, selection of hybridomas, cloning and scaling up of hybridomas, and purification of monoclonal antibodies are well described in handbooks for the generation of monoclonal antibodies e.g. Harlow and Lane, Antibodies: a laboratory manual, Cold Spring Harbor Laboratory 1988 or Coligan et al., Current Protocols in Immunology, John Wiley and Sons Inc. 1992.

Antigen-specific B cells can be selected and grown up under limiting dilution conditions in a culture system for B cells, preferably the EL-4 B-cell culture system. Then individual B-cell clones can be submitted to fusion in order to obtain monoclonal antibody producing hybridomas as described a.o. in EP448470 and U.S. Pat. No. 6,020,170 herein included by reference.

Human monoclonal antibodies or antibody fragments can also be generated according to techniques well known in the art. Chimerization or humanization of suitable mouse monoclonal antibodies can generate human antibodies or antibody fragments. Another well-known technique for generating human antibodies or antibody fragments is the phage display technology. Human monoclonal antibodies can also be generated by EBV-transformation of in vivo primed B cells, by immortalization of in vitro immunized B cells or by immortalization of B cells from immunized transgenic mice expressing a human immunoglobulin repertoire.

Immunization with the appropriate complex can be performed with MHC-peptide complex which is isolated as described in example 1. As a source of the complex, however, also antigen presenting cells (APC's) such as monocytes, dendritic cells and B-cells having the appropriate MHC complex and loaded with the specific autoantigen e.g. by providing APC's with HC gp-39, may be used. As an alternative to providing APC's with the complete protein of interest also subsequences thereof may be provided. The length of the subsequences is not important provided that it comprises the epitope to be recognized by the relevant MHC molecule. Preferably these peptides have an amino acid sequence of 9-55 amino acid residues. More preferably the peptides have an amino acid sequence of 9-35, in particular 9-25 amino acid residues. Much more preferred are peptides having an amino acid sequence of 9-15 amino acid residues. The most preferred peptide is HC-gp-39$^{263-273}$ or HC-gp-39$^{263-275}$.

Thus, it is also an object of the present invention to provide antibodies which are specific for MHC-peptide complexes associated with autoimmune diseases, preferably rheumatoid arthritis. Preferably, the MHC complex is of the type HLA DRB1*0401, DRB1*0404, DRB1*0407 and DRB1*0101, HLA DRB1*0401 being the most preferred whereas the peptide in the complex is preferably a RA associated antigen. The most preferred peptide is derived from HC gp-39. Preferably the peptide comprises the amino acids 263-273 or 263-275 of HC gp-39 (HC-gp39$^{263-273}$ or HC-gp39$^{263-275}$), but small variations in the amino acid sequences are possible. The most preferred antibodies are ORG38948 08A, ORG38948 12A or ORG38948 04B.

It is also an object of the present invention to provide antibodies reacting with specific MHC-peptide complexes wherein the peptide consists of multimers of a smaller RA associated peptide such as for example a dimer or trimer. A multimer can either be a homomer, consisting of a multitude of the same peptide, or a heteromer consisting of different peptides.

Again another object of the present invention is to provide antibodies reactive to autoimmune specific complexes, the peptide of which is connected to MHC molecules, such that the binding groove is occupied by the peptide. A flexible linker molecule, preferably also consisting of amino acid sequences might connect the peptide. Also the MHC subunits might be covalently linked either directly or through a flexible spacer molecule. They might be built on e.g. monomeric or dimeric Ig molecules as "scaffold". The MHC molecules do not need to possess their constant domains and might consist of their variable domains only, either directly covalently linked to each other or linked through a flexible linker. Such antibodies or fragments thereof can be prepared by conventional recombinant DNA technology. Dimeric MHC/peptide complexes with IgG as scaffold are a.o. described by Lebowitz et al. (1999) Cellular Immunology 192:175-184.

Tetrameric MHC/peptide complexes for MHCI have been described by Davis et al. (1996) Science 274:94-99 and for MHC II by Guitgemann et al. (1998) Immunity 8:667-673 and Kotzin et al. (2000) Proc. Natl. Acad. Sci. USA 97:291-296.

The antibodies of the present invention can be used for the identification of autoimmune specific complexes e.g. of HC gp39$^{263-275}$ on APC in tissue sections and quantification of MHC-peptide complexes e.g. DRB1*0401/HC gp39$^{263-275}$ complexes on individual APC's. Quantification of the MHC-peptide complex with specific antibodies provides an opportunity to monitor the disease activity. The antibodies can further be used to localize the APC's within pathological tissues.

Depending on the antibody i.e. the specificity of the MHC-peptide complex several autoimmune diseases such as insulin-dependent diabetes mellitus, multiple sclerosis, Myasthenia gravis, psoriasis or rheumatoid arthritis can be diagnosed. Furthermore, using antibodies with specificity for RA associated MHC-peptide complexes, rheumatoid arthritis can be distinguished from other causes of chronic inflammatory diseases such as polyarthritis, psoriatic arthritis, spondyloarthropathy or osteoarthritis.

There are several techniques for using the antibody or antibody fragments to detect specific MHC-peptide complexes. These techniques include but are not limited to: immunohistochemistry, FACS, immunoprecipitation and Western blot. The antibodies or antibody fragments can be used either unlabeled or conjugated to an enzyme, a radioactive isotype, a fluorochrome, a paramagnetic particle or a biotin molecule.

It is yet another object of the present invention to provide the antibodies for use in the purification of the MHC-peptide autoimmune complexes by e.g. affinity chromatography. For this purpose the antibodies are coupled to a solid matrix e.g. Sepharose beads, Silica beads or paramagnetic beads using techniques that are well-known in the art. The antibodies to be used for this purpose are those described for the diagnostic method according to the invention.

Moreover, such antibodies may be used to inhibit T-cell responses to autoantigenic peptides in vitro and in vivo.

It is another object of the present invention to provide antibodies to be used in therapy. The invention thus also provides a method to treat autoimmune diseases such as insulin-dependent diabetes mellitus, multiple sclerosis, psoriasis, Myasthenia gravis and rheumatoid arthritis, rheumatoid arthritis being the most preferred disease, by administration of the antibodies directed against the autoimmune complex, more specifically the MHC-peptide complex, preferably a MHC-HC gp-39 subsequence complex, more preferably a DRB1*0401, DRB1*0404, DRB1*0101 or DRB1*0407/HC gp39$^{263-273}$ or HC gp-39$^{263-275}$ complex. The antibodies ORG38948 08A, ORG38948 12A or ORG38948 04B are the most preferred antibodies. Variations of the antibodies as described before are also useful for therapeutic purposes. Thus, the monoclonal antibodies according to the invention can be used for the manufacture of a pharmaceutical for the treatment of autoimmune disorders, more preferably rheumatoid arthritis. Inflammation can be reduced by the administration of the antibodies according to the invention by blocking T-cell activation.

In order to avoid an antigenic response to the antibodies it is preferred to use human antibodies. If the antibodies are from non-human origin, humanized antibodies are preferred. Methods for humanizing antibodies, such as CDR-grafting, are known (Jones et al., Nature 321, 522-525, 1986).

The antibodies ORG38948 08A, ORG38948 12A or ORG38948 04B have been deposited at ECACC, Salisbury, Wiltshire SP4 0JG, UK under the accession numbers 99061728; 99061729 and 99061730, respectively. These deposits have been made under the terms of the Budapest Treaty.

The following examples are illustrative for the invention and should in no way be interpreted as limiting the scope of the invention.

LEGENDS TO THE FIGURES

FIG. 1 Monoclonal antibodies to Org38948 do not react with DRB1*0401 molecules.

Monoclonal antibodies were titrated on microelisa plates coated with purified Org38948 (a) or DRB1*0401 (b). Then the plates were incubated with goat anti-mouse-HRP and the color reaction was developed using standard ELISA procedures.

Figure 2:
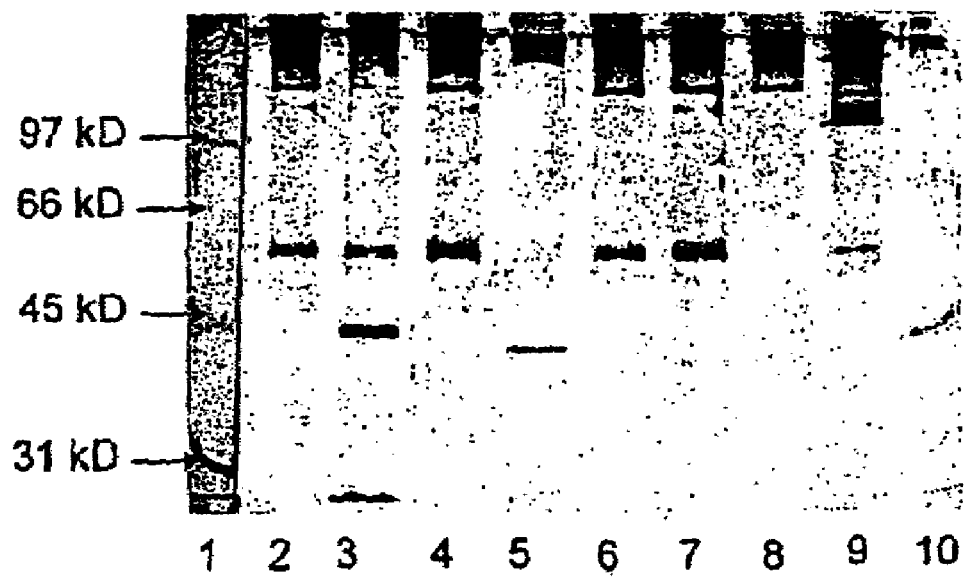
Figure 2:
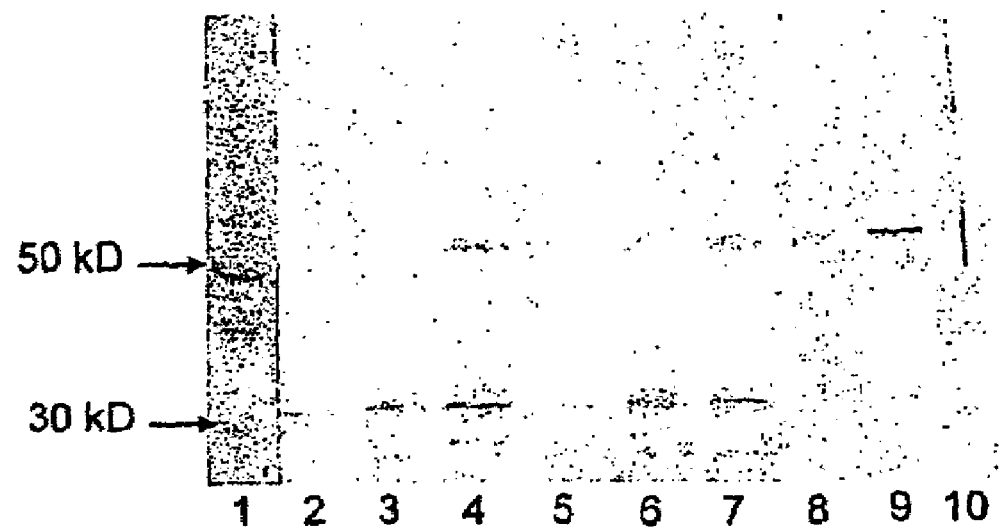

FIG. 2 Anti-Org38948 MAb recognize MHC class II molecules as determined by immunoprecipitation.

Top: blot 1; SDS/PAGE was performed under non-reducing conditions and blots were developed with L243. Bottom: Blot 2; SDS/PAGE was performed under reducing conditions and blots were developed wit L227.

Lane 1: molecular weight marker, lane 2:ORG38948 01A (IgG1, κ), lane 3: ORG38948 04B (IgA, κ), lane 4: ORG38948 08A (IgG1, κ), lane 5: ORG38948 09A (IgA, κ), lane 6: ORG38948 11B (IgG1, κ), lane 7: ORG38948 12A (IgG1, κ), lane 8: ZP(19-38) 1A (IgG1 control), lane 9: L243 (anti-HLA-DR), lane 10: ZP 1A (IgA control). Note: ORG38948 09A is an antibody that reacts with both Org38948 and DRB1*0401.

Figure 3A:
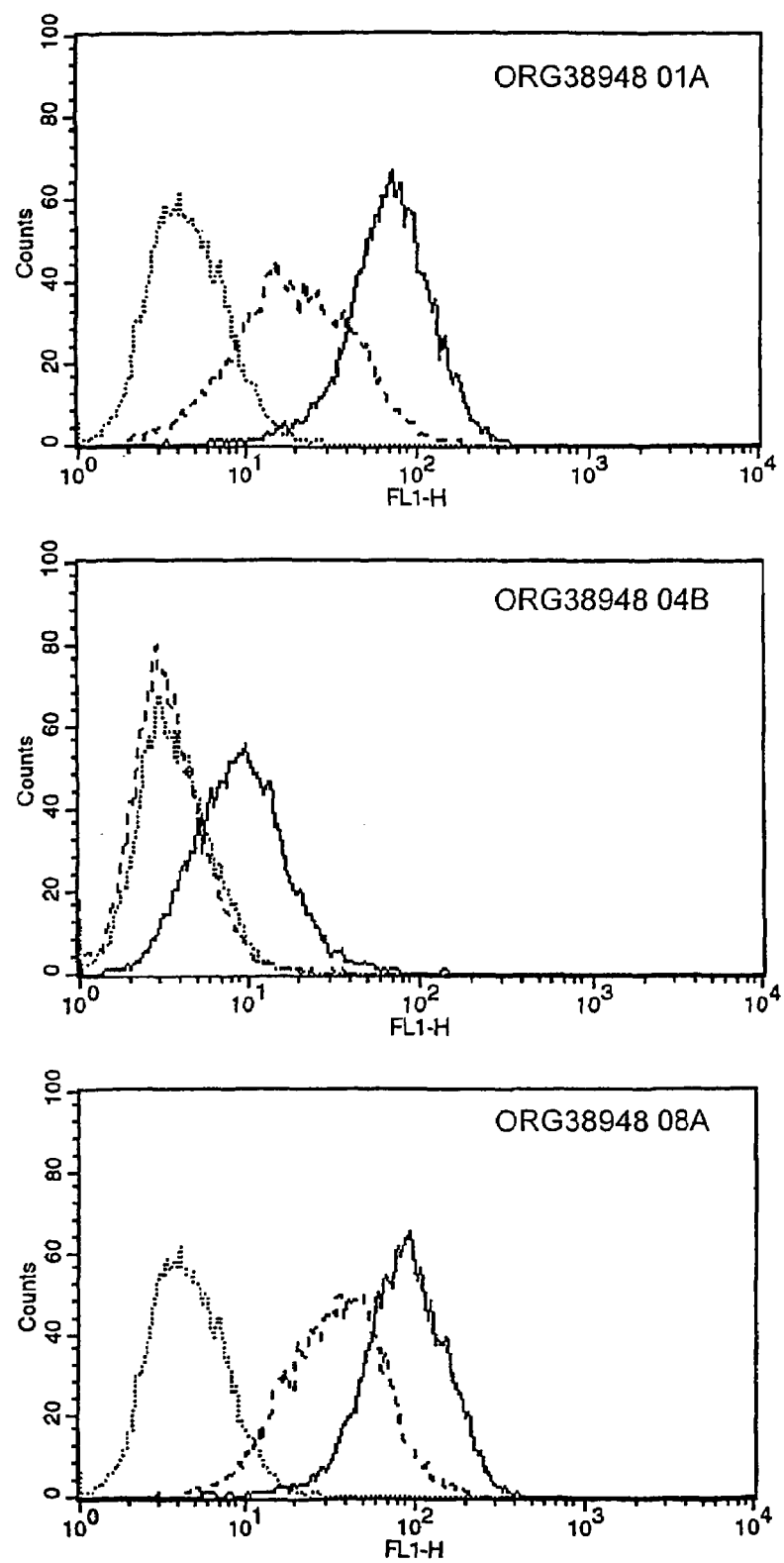
Figure 3A:
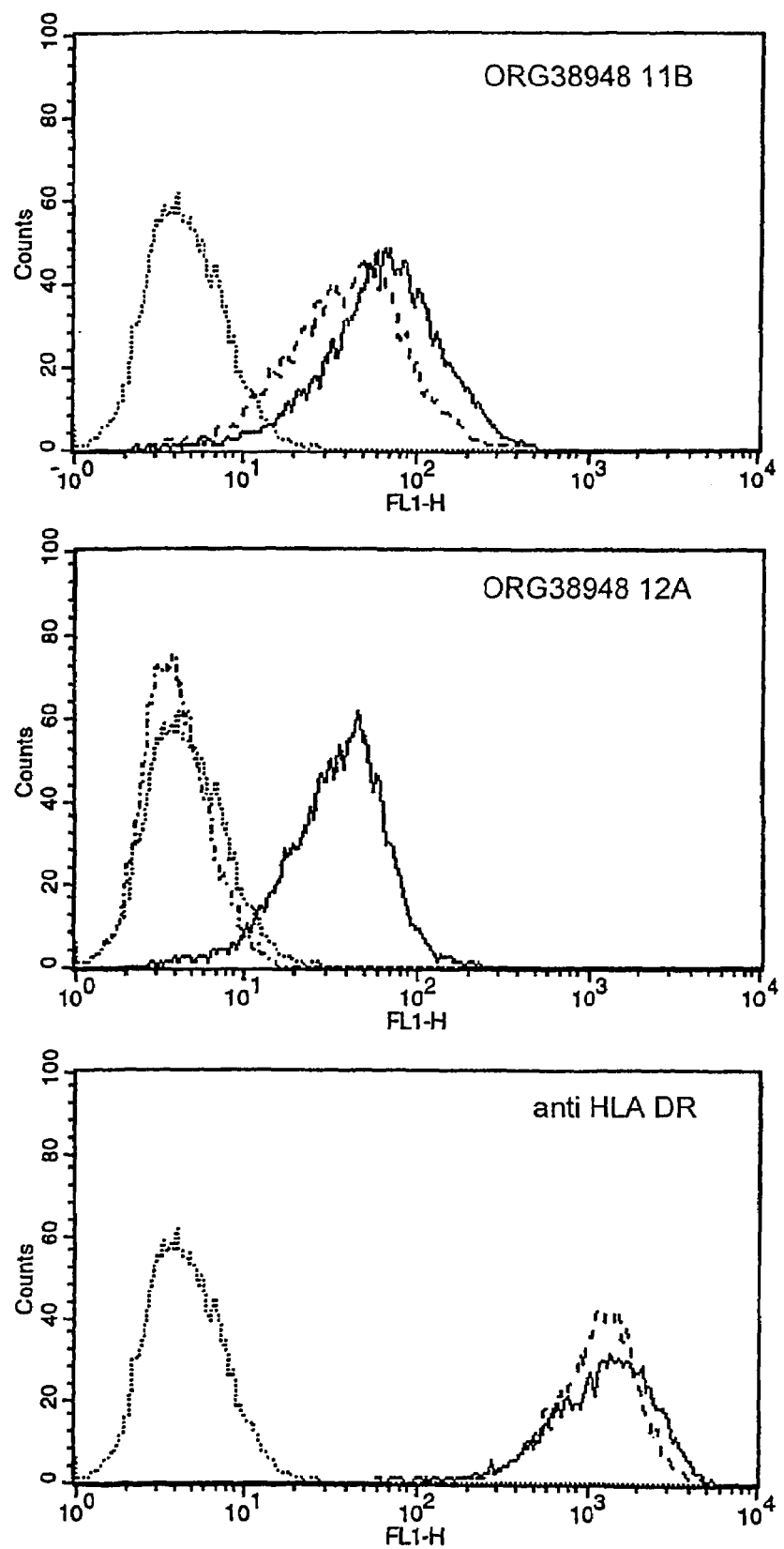

FIG. 3a Anti-Org38948 MAb recognize HC gp-39$^{263-275}$-complexes on DRB1*0401-positive BSM loaded with HC gp-39$^{263-275}$. BSM cells were loaded with HC gp-39$^{263-275}$ (———) and staining by anti-Org38948 antibodies was compared to staining of non-loaded cells (- - - - - - - -) by FACS analysis. Anti-HLA/DR, L243, was used as a positive control for the presence of DR-molecules. Isotype control antibodies were used as a negative control (················).

Figure 3B:
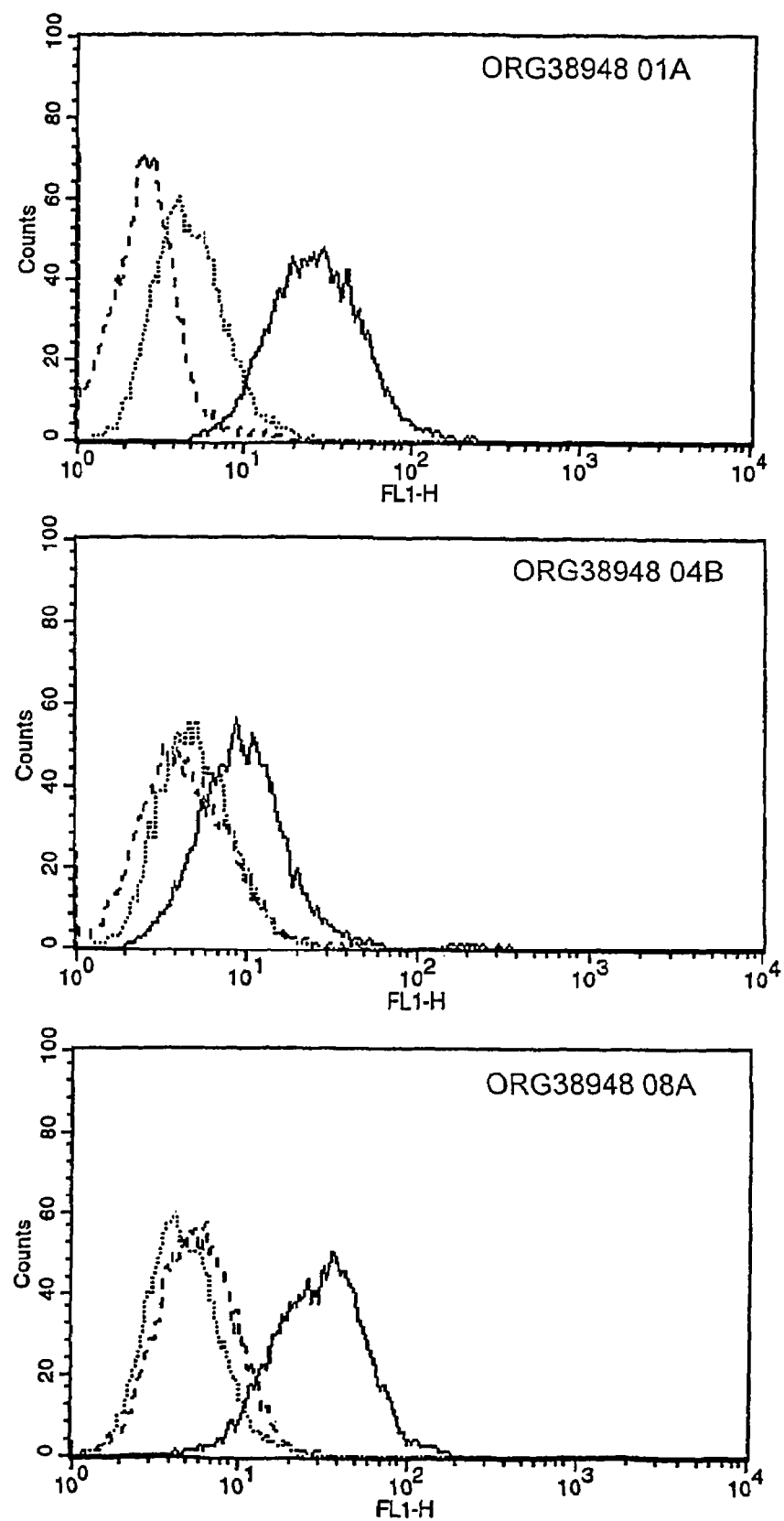
Figure 3B:
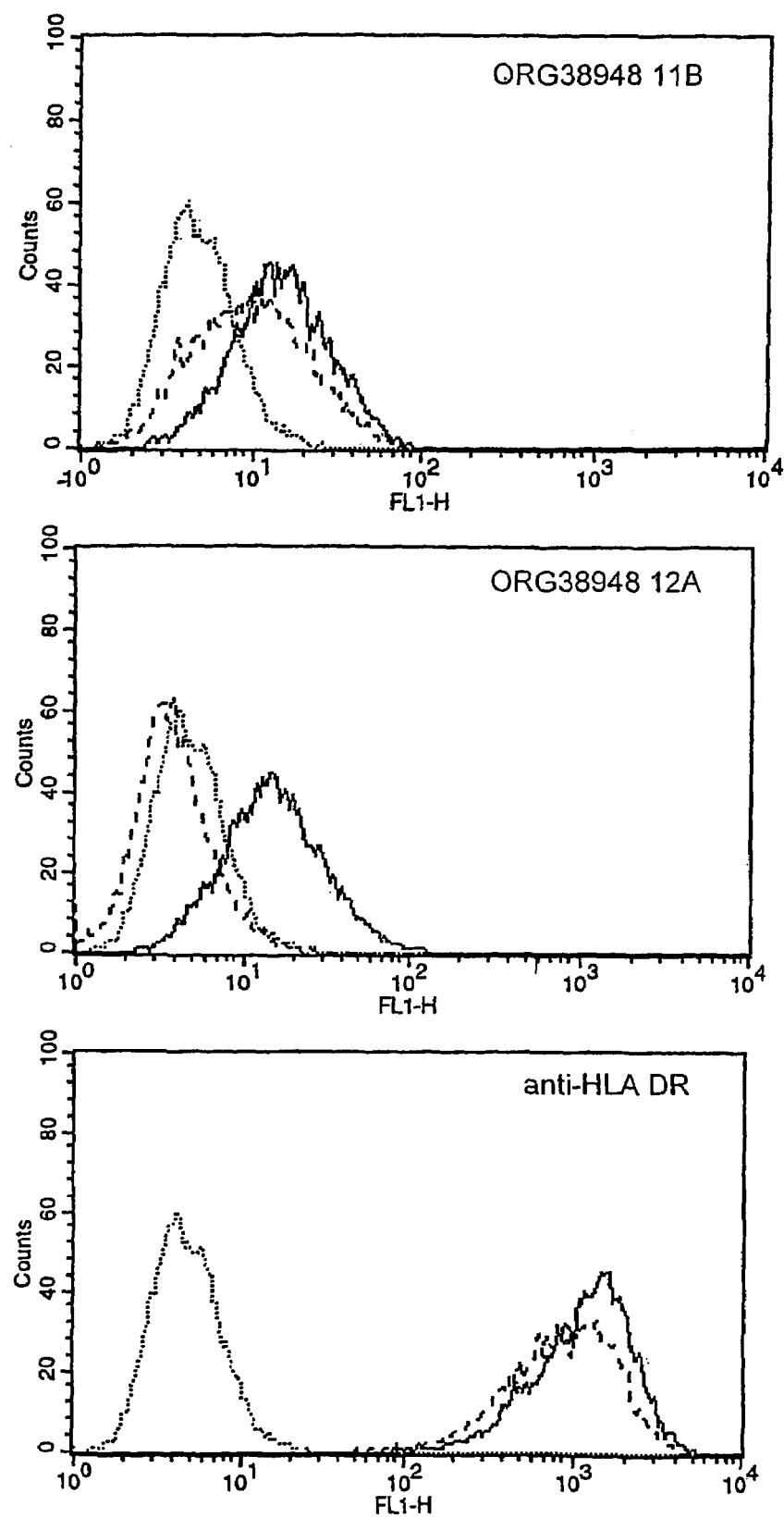

FIG. 3b: Anti-Org38948 MAb recognize HC gp-39$^{263-275}$-complexes on DRB1*0401-positive Priess loaded with HC gp-39$^{263-275}$. Priess cells were loaded with HC gp-39$^{263-275}$ (———) and staining by anti-Org38948 antibodies was compared to staining of non-loaded cells (- - - - - - - -) by FACS analysis. Anti-HLA/DR, L243, was used as a positive control for the presence of DR-molecules. Isotype control antibodies were used as a negative control (················).

Figure 4:
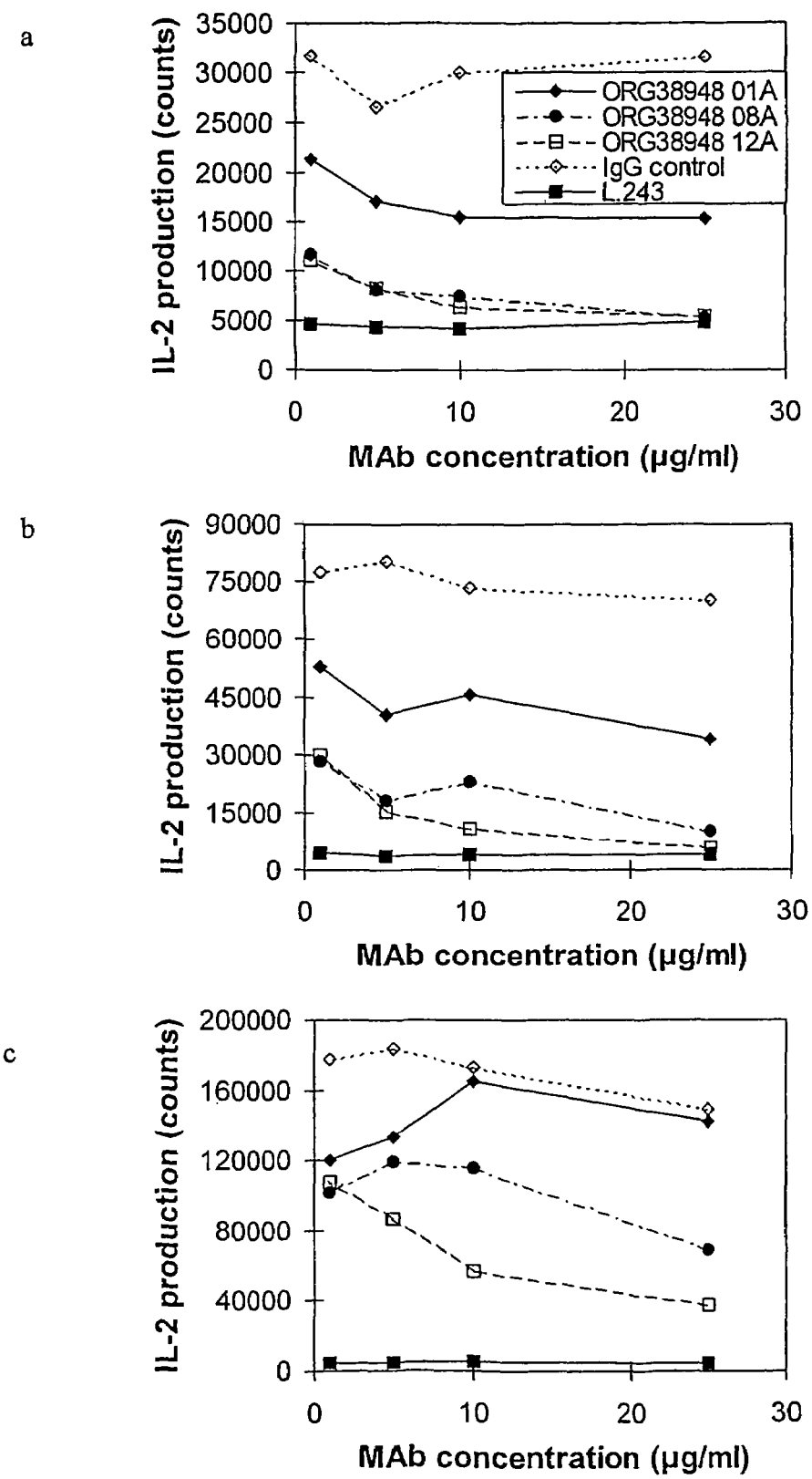

FIG. 4: Antibodies to Org38948 inhibit activation of T-cell hybridomas by Org38948.

Org38948 complexes were coated and incubated with increasing concentrations of MAb and the T-cell hybridoma of interest. After two days incubation at 37° C., IL-2 production was determined. Each value represents the mean counts of triplicate cultures. a) hybridoma 5G11, b) hybridoma 4G11 and c) hybridoma 8B12.

Figure 5:
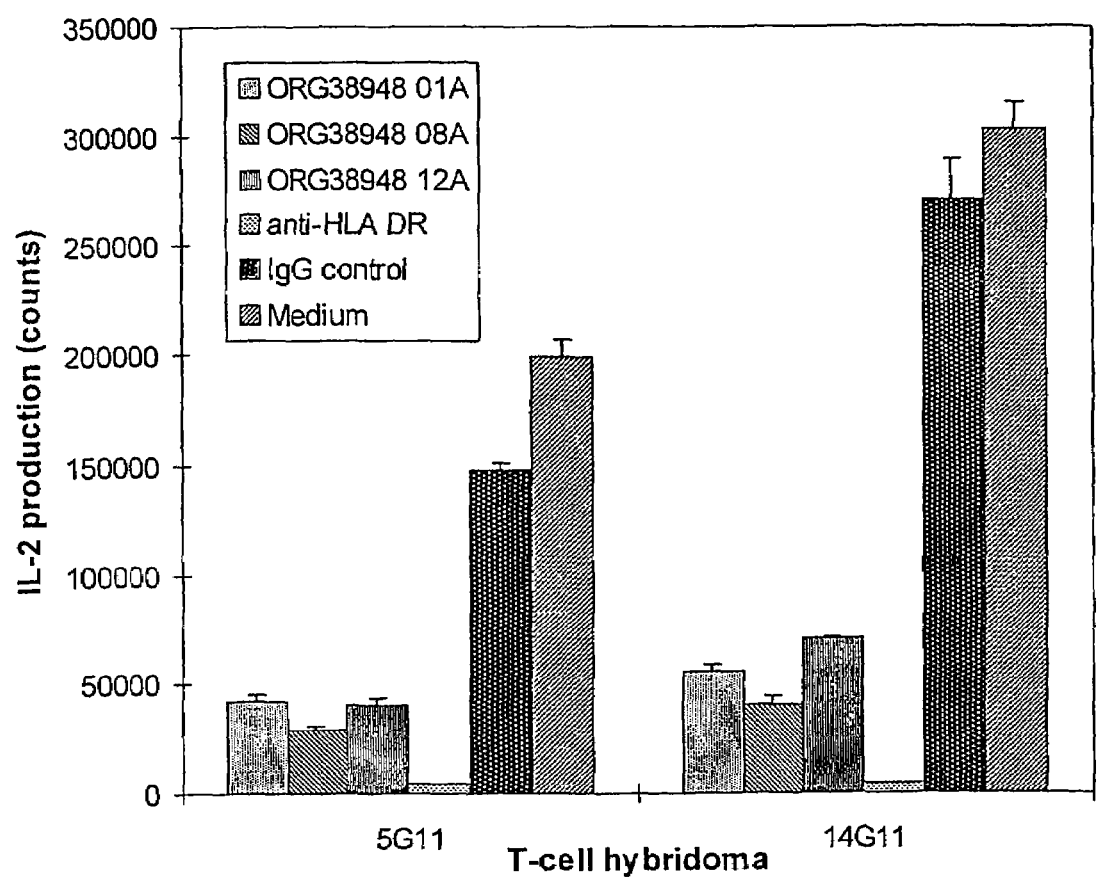

FIG. 5: Antibodies to Org38948 inhibit activation of T-cell hybridomas by BSM cells pulsed with HC gp-39$^{263-275}$. BSM cells pulsed with HC gp-39$^{263-275}$ were incubated with 10 µg/ml MAb and either T-cell hybridoma 5G11 (left panel) or 14G11 (right panel). After two days of incubation at 37° C., IL-2 production was determined. Each value represents the mean counts of triplicate cultures+ standard deviation.

EXAMPLES

Example 1

Production of Org38948

Org38948 is a complex of the DRB1*0401 (DRA, DRB1*0401) dimer with a peptide encompassing amino acids 263-275 of HC gp-39, solubilized in 0.05% dodecylmaltoside detergent solution.

DRB1*0401 molecules were purified as described by Nag et al. (J. Immunol. (1993) 150: 1558-1564) with some minor modifications. Briefly, the EBV transformed lymphoblastoid cell line BSM (NIGMS; GM06821) was cultured in RPMI 1640 medium containing 10% FCS, 2 g/l glucose, 4 mM L-glutamine. After harvesting the cells, DRB1*0401 molecules were extracted with 0.5% Triton X100 in PBS. Then, the lysate was clarified by filtration and further concentrated on a 10 kD ultrafiltration membrane. The concentrated Triton X100 lysate was applied onto L243 coupled Sepharose-4B column, and the bound DRB1*0401 was eluted in PBS, 0.05% dodecylmaltoside pH 11.3. Fractions were immediately neutralized with 20% sodium phosphate monobasic buffer, and the DRB1*0401 molecules were collected through a DEAE ion-exchange column in PBS, 0.05% dodecylmaltoside pH 7.3.

The peptide that corresponds to amino acid residues 263-275 of HC gp-39 was synthesized under GMP conditions at Diosynth using fmoc chemistry.

MHC-peptide complexes were prepared by incubating a 50× molar excess of HC gp-39$^{263-275}$ with purified DRB1*0401 molecules for 72-80 h at 37° C. in PBS, 0.05% dodecylmaltoside pH 7.0. Finally, free peptide was removed by S-300/S-200 tandem size exclusion column chromatography and purified complexes were stored in PBS, 0.05% dodecylmaltoside pH 7.2.

Example 2

Generation of Monoclonal Antibodies to Org38948

Six-week old female BALB/c mice were immunized according to the schedule presented in Table I. At day 48 of the immunization schedule, a blood sample was taken by orbita punction. At this time, high titers of antibodies to Org38948 and DRB1*0401 (ranging from 22,000 to 46,000) were found. No significant differences were found between the immunization schedules used. Five days after the final injection, mice were sacrificed and erythrocyte-depleted spleen cell populations were prepared as described previously (Steenbakkers, 1992 J. Immunol. Methods 152:69; Steenbakkers, 1994, Molecular Biology Reports 19:125). These spleen cell populations were either frozen at −140° C. or used for the generation of MAb directly.

For the generation of MAb, 2×10$^7$ erythrocyte-depleted spleen cells from mouse 1, mouse 2 and mouse 3 were pooled and incubated in DMEM/HAM's F12 (Gibco BRL, Paisly, UK, cat. no. 041-91825), 10% Calf Serum (Hyclone, Logan, Utah, USA) for 1 h at 37° C. on a plastic culture flask in order to remove the majority of monocytes. Subsequently, the non-adherent cells were submitted to three subsequent cycles of panning on DRB1*0401-coated culture dishes as described by Steenbakkers et al. (1994, Molecular Biology Reports 19:125). In those steps, B cells directed to HLA-DRB1*0401 are removed from the cell suspension. Subsequently, B cells directed to DRB1*0401/HC gp39$^{263-275}$-complexes were selected by incubating the resulting cell suspension on Org38948-coated culture dishes for 90 min at 37° C. Unbound cells were removed by careful washing and finally bound cells were harvested by trypsin treatment.

Monoclonal antibody producing hybridomas were generated from these selected B cells by clonal expansion and mini-electrofusion as described previously (Steenbakkers et al., 1994 Molecular Biology Reports 19:125). Briefly, selected B cells were mixed with T-cell supernatant and 50,000 irradiated (2500 rad) EL-4 B5 cells at a final volume of 200 µl DMEM/HAM's F12, 10% Calf Serum in 96-well flat bottomed tissue culture plates. On day 8, supernatants were tested in an ELISA using either DRB1*0401- or Org38948-coated plates. B-cell cultures producing MAb reactive with Org38948 and not with DRB1*0401 were submitted to a mini-electrofusion procedure. The specific B-cells from these cultures were mixed with 10$^6$ NS-1 myeloma cells and serum was removed by washing with DMEM/HAM's F12. Next, the cells were treated with pronase solution for 3 min and subsequently washed with fusion medium. Electrofusion was performed in a 50 µl fusion chamber by an alternating electric field of 30 s, 2 MHz, 400 V/cm followed by a square, high field pulse of 10 µs, 3 kV/cm and again an alternating electric field of 30 s, 2 MHz, 400 V/cm. Finally, the contents of the fusion chamber were transferred to selection medium (DMEM/HAM's F12, 10% FCS, 10$^{-4}$ M hypoxanthine (Sigma®), 1.6×10$^{-5}$ M thymidine (Sigma®), 0.4 µM aminopterin (Life Technologies®), 1% conditioned medium of human bladder carcinoma T24 (ATCC HTB 4)) and plated into a 96-well microtiter plate under limiting dilution conditions. At day 13 after fusion, the cultures were examined for hybridoma growth and screened again in an ELISA using either DRB1*0401- or Org38948-coated plates.

After B-cell culture and mini-electrofusion, 5 antibodies (ORG38948 01A, ORG38948 04B, ORG38948 08A, ORG38948 11B and ORG38948 12A) were found that showed reactivity with Org38948, but not with DRB1*0401 in an ELISA (FIGS. 1a and 1b). As these MAb also do not react with HC gp-39$^{263-275}$ coated on polystyrene plates, and because reactivity to Org38948 could not be inhibited by free HC gp-39$^{263-275}$, these MAb are directed to a combination epitope of DRB1*0401 and HC gp-39$^{263-275}$. Absence of binding to peptide HC gp-39$^{263-275}$ was confirmed in a BIAcore experiment.

To further support specificity of the MAb, we performed immunoprecipitations with Org38948. Briefly, 10 µg Org38948 were incubated with 6×10$^6$ Sheep anti-mouse Ig coupled paramagnetic beads (Dynal® 110.02, Oslo, Norway) preloaded with 1 ml hybridoma supernatant for 2 h at 4° C. in 300 µl PBS, 0.1% BSA. Then, immunoprecipitates were washed three times with PBS, boiled in sample buffer and submitted to SDS-PAGE on a 10% gel under non-reducing and reducing conditions. Electrophoretic transfer of the proteins to PVDF membranes was performed using standard procedures. After blocking free binding sites on the blots with PBS, 0.5% Tween20®, 5% skim milk, the blots were incubated with anti-DR MAb (either 20 ml L243 at 2 µg/ml or 12.5 ml L227 at 1.1 µg/ml) in PBS, 0.5% Tween20®, 1% BSA, 1% normal goat serum for 1 h at room temperature. Then, the blots were incubated for 1 h with alkaline phosphatase-conjugated goat anti-mouse Ig in the same buffer. Finally, the blots were developed using BCIP® and NBT as a chromogenic substrate. These experiments showed that the MAb are able to immunoprecipitate a molecule of 60 kD which dissociates into two molecules of 33 kD and 28 kD when run on a SDS/PAGE under reducing conditions (FIG. 2). These molecular weights confirm reactivity of the MAb to MHC class II molecules which consist of two non-covalently linked polypeptide chains (α-chain 32 kD and β-chain 28 kD).

Example 3

MAb to Org38948 recognize DRB1*0401/HC gp-39$^{263-275}$ complexes on DRB1*0401-positive BLCL loaded with HC gp-39$^{263-275}$.

Using FACS analysis, binding of the MAb to different MHC-expressing EBV-transformed B-cell lines (BLCL) pulsed with various peptides was established. Peptides were synthesized by solid phase peptide synthesis using an automated Milligen 9050 synthesizer and purified by reverse phase HPLC.

Briefly, 10$^6$ BLCL were incubated with 40 µg peptide in 500 µl DMEM/HAM's F12 or blank medium for 4 h at 37° C. After this incubation, the cells were washed with PBS, 2% FCS, 0.02% sodiumazide. Approximately 2×10$^5$ cells were incubated for 1 h, 4° C. with 130 µl MAb-containing hybridoma supernatant plus 20 µl PBS, 20% FCS, 0.02% sodiumazide. After washing the cells twice with PBS, 2% FCS, 0.02% sodiumazide, they were incubated for 1 h, 4° C. with 50 µl PBS, 20% FCS, 0.02% sodiumazide plus 10 µl Goat anti-mouseIg/FITC (Beckton & Dickinson). Subsequently, the cells were washed three times with PBS, 2% FCS, 0.02% sodiumazide and finally resuspended in 400 µl PBS, 2% p-formaldehyde. As a control for peptide binding, cells were incubated with biotinylated HC gp39$^{263-275}$ and stained with streptavidin/PE (Beckton & Dickinson). As a control for HLA-DR expression, staining was performed with anti-HLA/DR, L243 (purified Ig from hybridoma ATCC HB 55). Stained cells were analyzed with the FACScan™ (Beckton & Dickinson). In all cases, forward and side scatter analysis was applied to eliminate dead cells and debris from further analysis.

Two BLCL homozyous for DRB1*0401 (BSM and Priess) were loaded with HC gp-39$^{263-275}$, and reactivity of the antibodies to these cells was compared to cells that were not loaded with this peptide. FIGS. 3a and b shows that all Org38948-specific antibodies, except ORG38948 11B, discriminate in reactivity between peptide-loaded and non-loaded BLCL. The best staining of DRB1*0401/HCgp-39$^{263-375}$-complexes was obtained with ORG38948 01A, ORG38948 08A and ORG38948 12A. However, two of these antibodies (01A and 08A) showed some background staining on one of the BLCL (BSM), which probably makes them less useful.

Example 4

Epitope Mapping of MAb to Org38948

By studying binding to various modified and truncated peptides of HC gp-39$^{263-275}$ in the context of DRB1*0401, we mapped the epitopes recognized by the antibodies. Reactivity of the antibodies was compared with recognition by the TCR of mouse T-cell hybridoma 8B12 (mouse T-cell hybridoma recognizing HC gp-39$^{263-275}$ in the context of HLA-DRB1*0401. This hybridoma was generated from HLA-DRB1*0401$^{+/+}$, human CD4$^{+/+}$, I-Aβ$^{-/-}$ transgenic mice immunized with HC gp-39$^{263-275}$ as described by Cope et al., 1999 Arthritis and Rheumatism 42:1597-1507)

Various modifications in the peptide backbone and sidechains are allowed without influencing recognition by ORG38948 12A or 8B12 (Table II). Recognition by antibodies ORG38948 01A and ORG38948 08A appears more critical with respect to the epitopes recognized as the modifications are recognized less well (ORG38948 08A) or not at all (ORG38948 01A). ORG38948 12A does not react with a peptide that is elongated by two amino acids at the N-terminus (DRB1*0401/HC gp-39$^{261-275}$).

In another experiment, various truncations of HC gp-39$^{263-275}$ were tested in order to establish the minimal epitope in DRB1*0401 recognized by ORG38948 12A. At the C-terminus two amino acids can be removed without loss of binding, whereas at the N-terminus no truncations are allowed (Table III). So, the minimal epitope recognized by ORG38948 12A is DRB1*0401/HC gp-39$^{263-273}$. The epitope recognized by ORG38948 12A is different from the epitope recognized by hybridoma 8B12. Besides truncation of two amino acids at the C-terminus, hybridoma 8B12 allows removal of two amino acids at the N-terminus.

Example 5

Fine Specificity of MAb to Org38948

Using the same procedure as described in example 3, it was investigated whether 1) the anti-Org38948 MAb cross-react with DRB1*0401 loaded with a set of different peptides and 2) binding of ORG38948 12A is restricted to HC gp-39$^{263-275}$ in the context of DRB1*0401 or that other HLA-DR/HC gp-39$^{263-275}$-complexes are also recognized.

Ad 1) Priess cells were pulsed with peptides that bind well to DRB1*0401. The data summarized in Table IV show that no cross-reaction was observed with DRB1*0401 loaded with other HC gp-39-derived peptides that accomplish a DRB1*0401-binding motif. Also no cross-reaction was found with DRB1*0401 loaded with unrelated peptides from *Influenca Heamagglutinin* and *Mycobacterium Leprae*.

ORG38948 12A also recognizes biotinylated HC gp-39$^{263-275}$ whereas antibodies ORG38948 01A, ORG38948 04B and ORG38948 08A do not. As the biotin is coupled to the N-terminus of the peptide, this suggests that the latter MAb recognize an epitope closely to the N-terminus of the peptide in the complex.

Ad 2) To study the cross-reactivity of ORG38948 12A with other HLA-DR/HC gp-39$^{263-275}$-complexes than DRB1*0401/HC gp-39$^{263-275}$, the following well-characterized, homozygous EBV-transformed B lymphoblastoid cell lines (BLCL) were used:

Priess: DRA, DRB1*0401
BSM: DRA*0101, DRB1*0401, DRB4*0101, DQA1*0301, DQB1*0302, DPA1*01, DPB1*01012.
YAR: DRA*0101, DRB1*0402, DRB4*0101, DQA1*0301, DQB1*0302, DPA1*01, DPB1*0401
SA9001: DRA, DRB1*0101, DQ1, DP4.
BM92: DRA*0101, DRB1*0404, DRB4*0101, DQA1*0301, DQB1*0302, DPA1*01, DPB1*0402.
MGAR: DRA*0102, DRB1*1501, DRB5*0101, DQA1*0102, DQB1*0602, DPA1*01, DPB1*0401.
JHAF: DRB1*0407, DRB4*0101, DQA1*0301, DQB1*0301, DPA1*01, DPB1*0301.
AMALA: DRA*0102, DRB1*1402, DRB3*0101, DQA1*0501, DQB1*0301, DPA1*01, DPB1*0402.
EK: DRA*0102, DRB1*1401, DRB3*0202, DQA1*0101, DQB1*0503, DPA1*01, DPB1*0402.

These homozygous BLCL were loaded with HC gp-39$^{263-275}$ and subsequently stained with ORG38948 12A. In a series of experiments, ORG38948 12A stains HC gp-39$^{263-275}$ in the context of both DRB1*0401 and DRB1*0407 (Table V). At normal concentrations of antibody, no staining was observed of the peptide in the context of DRB1*0101, DRB1*0404, DRB1*1402 (RA susceptible haplotypes), DRB1*0402, DRB1*1301, DRB1*1401 (closely related, not RA susceptible haplotypes) and DRB1*1501 (more distantly related, not RA susceptible haplotype). At extremely high concentrations of antibody, also weaker reactivity was found with HC gp-39$^{263-275}$ in the context of DRB1*0101, DRB1*0404, DRB1*1301 and DRB1*1401. In the controls of these experiments, it was established that i) ORG38948 12A does not bind to non-loaded BLCL, ii) HC gp-39$^{263-275}$ binds to the BLCL and iii) all BLCL show a high level of DR-expression (data not shown).

Example 6

MAb to Org38948 Inhibit Activation of T-cell Hybridomas by Org38948 and DRB1*0401-Positive BLCL Pulsed with HC gp-39$^{263-275}$.

Inhibition of antigen-induced activation of T-cell hybridomas by anti-Org38948 MAb was measured in two different assays. In one assay, the T-cell hybridomas were stimulated with MHC/peptide-complexes. In the other assay EBV-transformed B cells loaded with HC gp-39$^{263-275}$ were used for stimulation of T-cell hybridomas 5G11, 8B12 and 14G11 (mouse T-cell hybridomas recognizing HC gp-39$^{263-275}$ in the context of HLA-DRB1*0401; these hybridomas were generated from HLA-DRB1*0401$^{+/+}$, human CD4$^{+/+}$, I-Aβ$^{-/-}$ transgenic mice immunized with HC gp-39$^{263-275}$ as described by Cope et al., 1999, Arthritis and Rheumatism 42:1597-1507)

For stimulation with MHC/peptide complexes, flat-bottomed microwells were coated overnight at 4° C. with 100 μl Org38948 at a concentration of 200 ng/ml in PBS. Excess complex was removed by washing twice with PBS. Then, the wells were incubated for 1 h at 37° C. with various concentrations of MAb in 100 μl DMEM/HAM's F12, 10% FCS. After preincubation with MAb, 100 μl T-cell hybridoma suspension in DMEM/HAM's F12, 10% FCS (5G11 and 14G11 at 2×10$^4$ c/well; 8B12 at 10$^4$ c/well) was added. Cultures were incubated for two days at 37° C. and finally supernatant was harvested for measurement of mouse IL-2. FIG. 4a shows that all MAb inhibited activation of hybridoma 5G11 in a dose-related fashion. Using ORG38948 01A, a partial inhibition was obtained as compared to a control IgG MAb. On the other hand, incubation with ORG38948 08A and ORG38948 12A resulted in complete inhibition at a concentration of 25 μg/ml. The complex-specific antibodies were less potent inhibitors of T-cell hybridoma activation than anti-HLA/DR MAb, L243, which may be due to differences in affinity of the antibodies. Similar results were obtained using hybridoma 14G11 (FIG. 4b). Hybridoma 8B12 was inhibited less well (FIG. 4c) which is in agreement with the our previous observations that this hybridoma requires less complexes to become fully stimulated.

In the other assay, BSM cells were loaded with HC gp-39$^{263-275}$ by incubation of 1.2×10$^6$ cells with 10 μg peptide in 1 ml DMEM/HAM's F12 for 5 h at 37° C. Then, excess peptide was washed out and the cells were irradiated with a dose of 15,000 rad.

Subsequently, 2×10$^4$ peptide-loaded BSM cells were pre-incubated for 1 h at 37° C. in round-bottomed microwells with 10 μg/ml of MAb in a final volume of 100 μl DMEM/HAM's F12. Then, 2×10$^4$ T-cell hybridomas were added in 100 μl DMEM/HAM's F12, 20% FCS. After two days incubation at 37° C., supernatant was harvested and tested on mouse IL-2. As can be deduced from FIG. 5, all antibodies were found to inhibit peptide-induced activation of hybridomas 5G11 and 14G11 at a concentration of 10 μg/ml. Again, stronger inhibition was obtained with anti-HLA/DR MAb, L243.

Note: Mouse IL-2 was determined in a double sandwich ELISA using anti-mouse IL-2 (Pharmingen 18161D) for capture and anti-mouse IL-2/biotin (Pharmingen 18172D) as a second antibody. Streptavidin conjugated to Europium (Wallac™ 1244-360) was used for detection of IL-2 binding in a time-resolved fluorometer.

Example 7

DRB1*0401/HC gp-39$^{263-275}$-complexes are Presented on APC in the Synovia of RA Patients Immunohistochemistry on synovial sections were performed as described by Baeten et al. (2000, Arthritis and Rheumatism 43:1233-1243). Briefly, synovial biopsies were snap frozen in liquid nitrogen and 5 μm cryostat sections were made. After fixation in acetone for 10 min and blocking of endogenous peroxidase with 1% hydrogen peroxide, the sections were incubated for 30 min with a pool of 3 different anti-HC gp-39 MAb (06A, 08B and 10B), or ORG38948 12A. Parallel sections were incubated with irrelevant isotype-matched MAb as a negative control. The sections were subsequently incubated with biotinylated anti-mouse secondary antibody, followed by a streptavidin-peroxidase complex (Dako, Glostrup, Denmark). The colour reaction was developed using 3-amino-9-ethylcarbazole (AEC) chromogen substrate. Finally, the sections were counter stained with haematoxylin. The stained synovial sections were blinded and scored independently by two observers.

Synovial tissue sections of 19 RA patients, 10 SpA patients, 3 PsA patients, 2 OA patients, 1 patient with chondrocalcinosis and 3 patients with an as yet unidentified diagnosis were tested on HC gp-39 expression and stained with ORG38948 12A by immunohistochemistry using a set of three anti-HC gp-39 MAb and ORG38948 12A respectively. DR4/HC gp-39$^{263-275}$ or DRB1*0101/HC gp-39$^{263-275}$-complexes were detected in 10 out of 15 shared epitope-positive RA patients (Table VIa). Reactivity with DRB1*0404/HC gp-39$^{263-275}$ and DRB1*0101/HC gp-39$^{263-275}$ is in agreement with the observation that ORG38948 12A also recognizes HC gp-39$^{263-275}$ in the context of DRB1*0404 and DRB1*0101 (Table V). Staining with ORG38948 12A was restricted to individual dendritic-like cells located in or nearby lymphoid infiltrates (data not shown). This location is clearly distinct from the location of the HC gp-39 expressing cells which suggests that MHC/HC gp-39$^{263-275}$ expressing cells are not the HC gp-39 producing cells. No staining with ORG38948 12A MAb was found in 19 control patients with various diseases (Table VIb). Five of these patients are relevant controls due to the expression of the shared epitope (DR4 or DR1), six are shared epitope-negative and the HLA-DR type of the others is still unknown. Staining with an isotype control antibody was always negative.

TABLE I

Immunizations with Org38948

| mouse no. | day 0 | day 20 | day 41 | Day 48 | day 59 | day 63 |
|---|---|---|---|---|---|---|
| 1 | 100 µg i.p. | 100 µg i.p. | 100 µg i.p. | Blood Sample | 100 µg i.p. | blood sample; spleen cells |
| 2 | 25 µg i.p. | 25 µg i.p. | 25 µg i.p. | Blood sample | 25 µg i.p. | blood sample; spleen cells |
| 3 | 100 µg cFA; s.c. | 100 µg iFA; s.c. | 100 µg iFA; s.c. | blood sample | 100 µg i.p. | blood sample; spleen cells |
| 4 | 25 µg cFA; s.c. | 25 µg iFA; s.c. | 25 µg iFA; s.c. | blood sample | 25 µg i.p. | blood sample; spleen cells | cFA = complete Freund's adjuvant;
iFA = incomplete Freund's adjuvant
i.p. = intraperitoneally;
s.c. = subcutaneously

TABLE II

Epitope mapping of monoclonal antibodies to Org38948

| | Recognition by | | | |
|---|---|---|---|---|
| HC gp-39 peptide | MAb 01A | MAb 08A | MAb 12A | 8B12 |
| RSFTLASSETGVG | + | + | + | + |
| Ac-RSFTLASSETGVG | − | − | + | + |
| HOCH2—(CHOH)4—CH2-RSFTLASSETGVG | +/− | +/− | + | + |
| Ac-RSFTLASSETGV-ψ-[CH2NH]-G-NH2 | − | +/− | + | + |
| Ac-R-NhSer-FTLASSETGVG-NH2 | − | +/− | + | + |
| Ac-R-NhSer-FTLASSETGV-ψ-[CH2NH]-G-NH2 | − | +/− | + | + |
| FGRSFTLASSETGVG | − | +/− | − | ? |
| Ac-RSFTLASSETGVG-NH2 | − | +/− | + | + |

TABLE III

Epitope mapping of monoclonal antibody ORG38948 12A

| | | Recognition by | |
|---|---|---|---|
| HC gp-39 peptide in DRB1*0401 | binding | MAb 12A | 8B12 |
| RSFTLASSETGVG | 263–275 | +++ | + | + |
| RSFTLASSETGV | 263–274 | +++ | + | + |
| RSFTLASSETG | 263–273 | +++ | + | +/− |
| RSFTLASSET | 263–272 | ++ | − | − |
| FTLASSETGVG | 265–275 | +++ | − | +/− |
| TLASSETGVG | 266–275 | − | − | − |
| SFTLASSETGV | 264–274 | +++ | − | + |
| FTLASSETG | 265–273 | + | − | − |

TABLE IV

Specificity of Org38948 MAb for DRA/DRB1*0401 on Priess cells loaded with different peptides.

| Peptide | IC50 | 01A | 04B | 08A | 11B | 12A |
|---|---|---|---|---|---|---|
| None | − | − | − | +/− | +/− | − |
| HC gp-39$^{263-275}$ | 0.08 | + | +/− | + | +/− | + |
| HC gp-39$^{263-275}$-bio | n.d. | − | − | +/− | +/− | + |
| HC gp-39$^{103-116}$ | 0.08 | − | − | +/− | +/− | − |
| HC gp-39$^{259-271}$ | 0.04 | − | − | +/− | +/− | − |
| IHA$^{307-319}$F | 0.56 | − | − | +/− | +/− | − |
| IHA$^{307-319}$F-bio | n.d. | − | − | +/− | +/− | − |
| MLep 18K$^{38-51}$ | 0.3 | − | − | +/− | +/− | − |

IC50: releative binding affinity for DRB1*0401;
IHA: Influenca Haemagglutinin;
MLep; *Mycobacterium Leprae*
−: no binding of antibody (fluorescence intensity: 0–4)
+/−: intermediate binding of antibody (fluoresence intensity: 4–40)
+: strong binding of antibody (fluorescence intensity: 40–400)

TABLE V

Recognition of HLA-DR molecules loaded with HC gp-39$^{263-275}$ by monoclonal antibody ORG38948 12A

| | | | suscep- | Recognition by ORG38948 12A | |
|---|---|---|---|---|---|
| BLCL | HLA DR haplotype | | tibility for RA- | 3 µg/ml | 200–500 µg/ml |
| BSM | DRB1*0401 | DR4 Dw4 | susceptible | ++ | ++ |
| Priess | DRB1*0401 | DR4 Dw4 | susceptible | ++ | ++ |
| SA 9001 | DRB1*0101 | DR1 Dw1 | susceptible | − | +/− |
| BM92 | DRB1*0404 | DR4 Dw14 | susceptible | − | + |
| AMALA | DRB1*1402 | DR6 Dw16 | susceptible | − | − |

TABLE V-continued

Recognition of HLA-DR molecules loaded with HC gp-39$^{263-275}$ by monoclonal antibody ORG38948 12A

| BLCL | HLA DR haplotype | | susceptibility for RA- | Recognition by ORG38948 12A | |
|---|---|---|---|---|---|
| | | | | 3 µg/ml | 200–500 µg/ml |
| YAR | DRB1*0402 | DR4 Dw10 | closely related; not susceptible | – | – |
| CB6B | DRB1*1301 | DR6a | closely related; not susceptible | – | +/– |
| EK/OH | DRB1*1401 | DR6b | closely related; not susceptible | – | +/– |
| MGAR | DRB1*1501 | DR2 Dw2 | not susceptible | – | – |
| JHAF | DRB1*0407 | DR4 Dw13 | unknown | ++ | ++ |

Various BLCL were loaded with HC gp-39$^{263-275}$ and subsequently stained with ORG38948 12A. In the controls, it was established that i) ORG38948 12A does not bind to non-loaded BLCL, ii) HC gp-39$^{263-273}$ binds to the BLCL and iii) all BLCL show a high level of DR-expression.

TABLE VIa

Expression MHC/HC gp-39$^{263-275}$-complexes in synovium of RA patients.

| patient | age | diagnosis | disease duration | HLA-DR | MHC-peptide |
|---|---|---|---|---|---|
| 1 | 57 | RA | 1 year | B1*0404 | + |
| 2 | 74 | RA | 2 years | B1*0401 | – |
| 3 | 53 | RA | 6 years | B1*0401 | + |
| 4 | 60 | RA | 7 years | B1*0401 | + |
| 5 | 67 | RA | 19 years | B1*0101 | – |
| 6 | 78 | RA | 20 years | B1*0401 | – |
| 7 | 70 | RA | 22 years | B1*0401 | + |
| 8 | 64 | RA | 25 years | B1*0101 | – |
| 9 | 50 | RA | 2 months | B1*04 | + |
| 10 | 39 | RA | 3 months | ? | – |
| 11 | 50 | RA | 4 months | B1*04 | – |
| 12 | 52 | RA | 9 months | B1*04 | + |
| 13 | 24 | RA | 1 year | B1*0101 | + |
| 14 | 33 | RA | 3 years | B1*04 | + |
| 15 | 82 | RA | 4 years | ? | – |
| 16 | 48 | RA | 6 years | B1*0401, B1*0404 | + |
| 17 | 36 | RA | 8 years | –/– | – |
| 18 | 64 | RA | 15 years | ? | – |
| 19 | 58 | RA | 20 years | B1*04 | + |

RA: Rheumatoid Arthritis

TABLE VIb

Expression MHC/HC gp-39$^{263-275}$-complexes in synovium of non-RA controls.

| patient | age | Diagnosis | disease duration | HLA-DR | MHC-peptide |
|---|---|---|---|---|---|
| 1 | 30 | SpA | 2 months | ? | – |
| 2 | 36 | SpA | 3 months | –/– | – |
| 3 | 37 | SpA | 6 months | ? | – |
| 4 | 56 | SpA | 6 months | B1*0401 | – |
| 5 | 28 | SpA | 6 months | –/– | – |
| 6 | 52 | SpA | 8 months | –/– | – |
| 7 | 19 | SpA | 9 months | –/– | – |
| 8 | 22 | SpA | 2 years | B1*0401 | – |
| 9 | 35 | SpA | 3 years | ? | – |
| 10 | 41 | SpA | 12 years | B1*0401 | – |
| 1 | 48 | PsA | 1 month | ? | – |
| 2 | 60 | PsA | 1 month | –/– | – |
| 3 | 52 | PsA | 2 years | ? | – |
| 1 | 73 | CC | 2 years | –/– | – |
| 2 | 76 | OA | | | – |
| 3 | 66 | OA | | | – |
| 4 | 67 | ? | 9 months | B1*04 | – |
| 5 | 80 | ? | 1 month | ? | – |
| 6 | 38 | ? | 30 years | B1*0101 | – |

CC: chondrocalcinosis;:
SpA: spondyloarthropathy;
PsA: psoriatic arthritis;
OA: osteoarthritis

I claim:

1. A method for diagnosing rheumatoid arthritis, comprising detecting the presence of a rheumatoid arthritis specific MHC-peptide complex in a patient with antibodies, or antigen binding domains thereof, which specifically bind to a MHC-HC-gp39-derived peptide complex and do not specifically bind to the HC-gp39-derived peptide or the MHC alone.

2. The method of claim 1, wherein the MHC part of the complex is of the type selected from the group consisting of HLA DRB1*0401, DRB1*0404, DRB1*0407 and DRB1*0101.

3. The method of claim 2 wherein the MHC type is HLA DRB1*0401.

4. The method of claim 1 wherein the HC-gp-39 derived peptide comprises HC-gp39$^{263-273}$ or HC-gp39$^{263-275}$.

5. The method of claim 4, wherein the HC-gp-39 derived peptide is HC-gp39$^{263-273}$ or HC-gp39$^{263-275}$.

6. The method of claim 5, wherein the antibody specifically binding to the MHC-HC-gp39-derived peptide complex is selected from the group consisting of the antibodies produced by hybridoma accession number 99061728, hybridoma accession number 99061729, and hybridoma accession number 99061730.

7. An antibody, or an antigen binding domain thereof, which specifically binds to a complex of HC-gp39-derived-peptide in the binding groove of an MHC molecule and does not specifically bind to the HC-gp39-derived-peptide or the MHC molecule alone.

8. A diagnostic composition comprising one or more of the antibodies or antigen binding domains thereof according to claim 7 and a detection agent.

9. A composition comprising the antibody or an antigen binding domain thereof of claim 7 and a pharmaceutically acceptable carrier and/or diluent.

10. The antibody or an antigen binding domain thereof of claim 7, wherein the MHC molecule is of the type selected from the group consisting of HLA DRB1*0401, DRB1*0404, DRB1*0407 and DRB1*0101.

11. The antibody or an antigen binding domain thereof of claim 10, wherein the MHC molecule is of the type HLA DRB1*0401.

12. The antibody or an antigen binding domain thereof of claim 7, wherein the HC-gp-39-derived-peptide comprises HC-gp39$^{263-273}$ or HC-gp39$^{263-275}$.

13. The antibody or an antigen binding domain thereof of claim 7, wherein the HC-gp-39-derived-peptide is HC-gp39$^{263-273}$ or HC-gp39$^{263-275}$.

14. The antibody or an antigen binding domain thereof of claim 7, wherein the antibody is selected from the group consisting of the antibodies produced by hybridoma accession number 99061728, hybridoma accession number 99061729, and hybridoma accession number 99061730.

* * * * *